United States Patent [19]
Kiesz

[11] Patent Number: 6,132,417
[45] Date of Patent: *Oct. 17, 2000

[54] RIGHT CORONARY ARTERY CATHETER

[75] Inventor: R. Stefan Kiesz, San Antonio, Tex.

[73] Assignee: Scheider/Namic, Glens Falls, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 09/136,847

[22] Filed: Aug. 19, 1998

Related U.S. Application Data

[60] Provisional application No. 60/058,947, Aug. 22, 1997.

[51] Int. Cl.$^7$ .................................................. A61M 25/00
[52] U.S. Cl. ......................... 604/523; 604/530; 604/532; 604/264
[58] Field of Search .................................. 604/523, 530, 604/532, 264, 500, 507, 508

[56] References Cited

U.S. PATENT DOCUMENTS

| | | | |
|---|---|---|---|
| 4,846,814 | 7/1989 | Ruiz | 604/281 |
| 4,961,731 | 10/1990 | Bodicky et al. | 604/264 |
| 5,195,990 | 3/1993 | Weldon | 604/281 |
| 5,215,540 | 6/1993 | Anderhub | 604/281 |
| 5,231,994 | 8/1993 | Harmjanz | 128/772 |
| 5,290,229 | 3/1994 | Paskar | 604/95 |
| 5,299,574 | 4/1994 | Bower | 128/658 |
| 5,304,131 | 4/1994 | Paskar | 604/95 |
| 5,306,262 | 4/1994 | Weldon | 604/281 |
| 5,306,263 | 4/1994 | Voda | 604/281 |
| 5,322,509 | 6/1994 | Rickerd | 604/53 |
| 5,348,545 | 9/1994 | Shani et al. | 604/281 |
| 5,401,258 | 3/1995 | Voda | 604/281 |
| 5,599,325 | 2/1997 | Ju et al. | 604/282 |
| 5,846,229 | 12/1998 | Berg | 604/281 |

FOREIGN PATENT DOCUMENTS

| | | |
|---|---|---|
| 0 728 494 | 8/1996 | European Pat. Off. . |
| WO 93/21983 | 11/1993 | WIPO . |
| WO 97/09087 | 3/1997 | WIPO . |

OTHER PUBLICATIONS 6 pages with illustrations of catheter shapes known as Judkins Left, Judkins Left Short Tip, Judkins Left Warren, Multipurpose, Amplatz Left, Internal Mammary, Brachial, Kimny, Judkins Right, Straight, Crossover, Cobra renal, Hockey Stick, 40°, Celiac and Superior Mesenteric Arteries (undated).

Guidant ACS Viking Guilding Catheter data sheets (4 pages), 1997.

*Primary Examiner*—John D. Yasko
*Attorney, Agent, or Firm*—Faegre & Benson LLP

[57] ABSTRACT

A right coronary artery catheter including a hub, a linear flexible tubular body stock extending from the hub and a curved flexible tubular stem extending from the body stock. The stem includes a distal end, a primary curved section and a secondary curved section. The primary curved section is positioned between the distal ends of the stem and body stock. The secondary curved section is positioned between the primary curved section and the distal end of the body stock, and extends in a direction generally opposite the direction of the primary curved section. The radii and lengths of the stem are adapted to cause a portion of the stem between the secondary curved section and the distal end of the body stock to engage a continuous length of the upper wall of the aortic arch, to cause the secondary curved section to direct the stem generally downwardly and across the ascending aorta toward a contralateral wall opposite the ostium of the right coronary artery, and to cause the primary curved section to engage the contralateral wall at a location adjacent to the ostium of the left coronary artery and to direct an end section of the stem across the ascending aorta toward the ostium of the right coronary artery, when the catheter is positioned within the patient with the distal end of the stem engaged with the ostium of the right coronary artery.

32 Claims, 8 Drawing Sheets

RIGHT CORONARY ARTERY CATHETER

REFERENCE TO RELATED APPLICATION

This application claims the benefit of U.S. Provisional Application Ser. No. 60/058,947 filed on Aug. 22, 1997.

BACKGROUND OF THE INVENTION

1. Field of the Invention

The present invention relates generally to coronary catheters. In particular, the present invention is catheter for use in connection with medical procedures on the right coronary artery.

2. Description of the Related Art

Catheters used in connection with medical procedures on the coronary system are generally known and disclosed, for example, in the following U.S. patents, all of which are hereby incorporated by reference in their entirety and for all purposes:

Inventor Patent No.

Voda U.S. Pat. No. 5,401,258
Shani et al. U.S. Pat. No. 5,348,545
Rickerd U.S. Pat. No. 5,322,509
Voda U.S. Pat. No. 5,306,263
Weldon U.S. Pat. No. 5,306,262
Paskar U.S. Pat. No. 5,304,131
Bower U.S. Pat. No. 5,299,574
Paskar U.S. Pat. No. 5,290,229
Harmjanz U.S. Pat. No. 5,231,994
Anderhub U.S. Pat. No. 5,215,540
Weldon U.S. Pat. No. 5,195,990
Bodicky et al. U.S. Pat. No. 4,961,731
Ruiz U.S. Pat. No. 4,846,814

Coronary catheters of the type described in the above-identified patents typically include an elongated and flexible tubular member mounted to a hub. The tubular member includes a relatively long and generally straight section sometimes referred to as the body stock which extends from the hub, and a nonlinear or curved section sometimes referred to as the stem which extends from the body stock. The distal end of the stem is often terminated with a tip.

The size, flexibility and other characteristics of catheters will vary depending upon their intended use. One particular type of catheter used for catheterization of the right coronary artery is known as a right coronary catheter. Right coronary catheters are inserted tip first into the femoral, brachial or radial artery of the patient and directed upwardly through the aorta until the tip is positioned adjacent to and engaged with the ostium or opening of the right coronary artery. During this catheterization procedure the tip of the catheter passes in sequence through the descending aorta, the aortic arch and the ascending aorta. Once it has been inserted, the catheter can be used for a wide variety of medical procedures. By way of example, interventional devices such as stents, rotational and directional atherectomy devices, guidewires and other devices can be deployed to the right coronary artery through the lumen of the catheter. Catheters of this type can also be used to guide and support balloon dilation catheters for percutaneous transluminal coronary angioplasty (PTCA) or percutaneous transluminal peripheral angioplasty (PTA), and for injecting dyes and other contrast media into the artery in connection with these procedures.

To be efficacious, right coronary catheters must be capable of being quickly inserted and removed from the aorta. The catheters must also be capable of accurately positioning their tips at the ostium of the artery being treated, without suddenly extending into and damaging the artery, a characteristic known as diving. The catheter must provide a back-up support since after it is inserted, a force known as the deployment force will be exerted on the interventional device being directed to the artery through the catheter. Without sufficient back-up support insertion of an interventional device may not be possible and trauma to the body vessels or ostium may occur. It is desirable that the inserted catheter be capable of retaining its position to allow the interventional device to be accurately deployed within the artery, even if relatively high deployment force is required. The catheter should, of course, be capable of providing these characteristics and properties while avoiding damage to the body vessels through which it is directed.

The shape of the catheter stem is an important factor contributing to the overall success of the procedures described above. Decisions on whether a given device can be delivered to a treatment site and the procedure successfully performed often depend upon the ability to appropriately catheterize the patient. There is, therefore, a continuing need for catheters having improved stem shapes.

SUMMARY OF THE INVENTION

The present invention is a right coronary catheter which can be efficiently inserted into and removed from the ostium of a patient's right coronary artery through the descending aorta, aortic arch and ascending aorta. The catheter can also be positioned in the ostium of the right coronary artery with a relatively high degree of accuracy.

One embodiment of the catheter comprises a flexible and tubular body stock and a flexible and tubular stem extending from a distal end of the body stock. The stem includes a distal end, a primary curved section and a secondary curved section. The primary curved section has one or more free state radii and a free state arc length, and is positioned between the distal ends of the stem and body stock. The secondary curved section has one or more free state radii and a free state arc length, is positioned between the primary curved section and the distal end of the body stock, and extends in a direction generally opposite the direction of the primary curved section. The radii and lengths of the stem including the primary and secondary curved sections are adapted to cause a portion of the stem between the secondary curved section and the distal end of the body stock to engage a continuous length of the upper wall of the aortic arch, to cause the secondary curved section to direct the stem generally downwardly and across the ascending aorta toward a contralateral wall opposite the ostium of the right coronary artery, and to cause the primary curved section to engage the contralateral wall at a location adjacent to the ostium of the left coronary artery and to direct an end section of the stem across the ascending aorta toward the ostium of the right coronary artery, when the catheter is positioned within the patient with the distal end of the stem engaged with the ostium of the right coronary artery.

DETAILED DESCRIPTION OF THE PREFERRED EMBODIMENTS

Figures 1, 2:
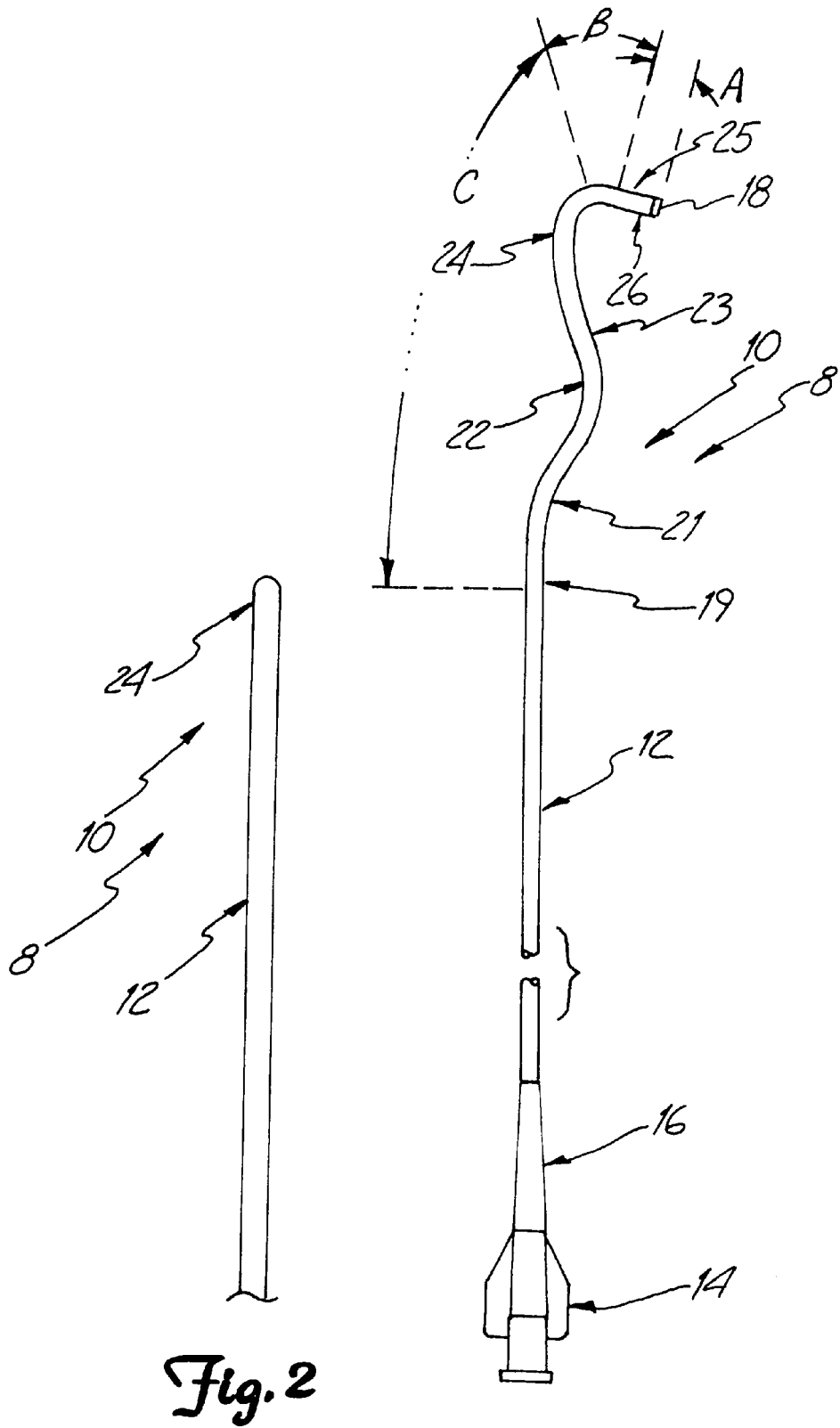
FIG. 1 is an illustration of a right coronary catheter having a nonlinear stem in accordance with the present invention.
FIG. 2 is a detailed side view of the catheter shown in FIG. 1, taken from the left side of FIG. 1.

A femoral approach right coronary artery catheter 8 which includes a tubular stem 10 in accordance with the present invention is illustrated generally in FIGS. 1 and 2. As shown, stem 10 extends from the distal end of an elongated flexible tubular body stock 12. A hub 14 is attached to a proximal end of the body stock 12 by means of a strain relief 16. A relatively soft tip 18 is positioned on the distal end of stem 10 in the embodiment shown. As described in greater detail below, the shape of stem 10 enables the catheter 8 to be efficiently inserted and its distal end (e.g., tip 18) accurately and coaxially positioned in the ostium of the right coronary artery. Once positioned, the stem 10 engages the contralateral wall of the ascending aorta at a location above and adjacent to the left coronary artery, and extends to the ostium of the right coronary artery without substantial engagement with or pressure on the right and/or left aortic valve cusps. This positional configuration enables the catheter to provide superior back-up support during the deployment of interventional devices.

Six embodiments of stem 10 are shown in greater detail in their free states in FIGS. 3–8, with no internal or external forces applied thereto. In each of the illustrated embodiments, the stem 10 includes a first arcuate section 21, a second arcuate section 22, a third linear section 23, a fourth arcuate section 24, a fifth arcuate section 25, and a sixth linear section 26 which includes tip 18. Stem 10 also includes a linear section 19 between first arcuate section 21 and body stock 12.

First arcuate section 21 is positioned between the generally linear body stock 12 and tip 18 (i.e., is positioned between the body stock and distal end of stem 10, and is distally disposed from the body stock), and has a first free state arc length A1 and a first free state radius R1. In the embodiment shown, first section 21 extends from and is contiguous with the linear section 19 of the stem 10, having a proximal end connected directly to the distal end of the linear section of the stem. Second arcuate section 22 is positioned between first section 21 and tip 18 (i.e., is distally disposed from the first arcuate section), and has a second free state arc length A2 and a second free state radius R2. In the embodiment shown, second arcuate section 22 extends from and is contiguous with first arcuate section 21, having a proximal end connected directly to the distal end of the first arcuate section. Third linear section 23 extends between second arcuate section 22 and tip 18 (i.e., is distally disposed from the second arcuate section), and has a free state length L3. In the embodiment shown, third linear section 23 is contiguous with and extends from section 22, having a proximal end connected directly to the distal end of the second section. Fourth arcuate section 24 is positioned between the third linear section 23 and tip 18 (i.e., is distally disposed from the third section), and has a fourth free state arc length A4 and a fourth free state radius R4. In the embodiment shown, fourth section 24 extends from and is contiguous with third section 23, having a proximal end connected directly to the distal end of the third linear section. Fifth arcuate section 25 is positioned between the fourth linear section 24 and tip 18 (i.e., is distally disposed from the fourth section), and has a fifth free state arc length A5 and a fifth free state radius R5. In the embodiment shown, fifth section 25 extends from and is contiguous with fourth section 24, having a proximal end connected directly to the distal end of the fourth arcuate section. Sixth linear section 26 extends from fifth arcuate section 25 (i.e., is distally disposed from the fifth arcuate section), and has a free state length L6 which includes the length of tip 18. In the embodiment shown, sixth linear section 26 is contiguous with and extends from section 25, having a proximal end connected directly to the distal end of the fifth section.

FIG. 2 is a side view of the body stock 12 and stem 10, and is taken from the side of the body stock opposite that of the tip 18 (i.e., from the left side of the body stock as illustrated in FIGS. 1 and 3–7). As is evident from FIG. 2, sections 21–26 and tip 18 of stem 10 are oriented in the same plane with one another and with the body stock 12 of the catheter 8. In other embodiments (not shown) sections 21–26 and tip 18 can extend (typically to a relatively limited extent) out of the planar configuration described above.

Figure 3:
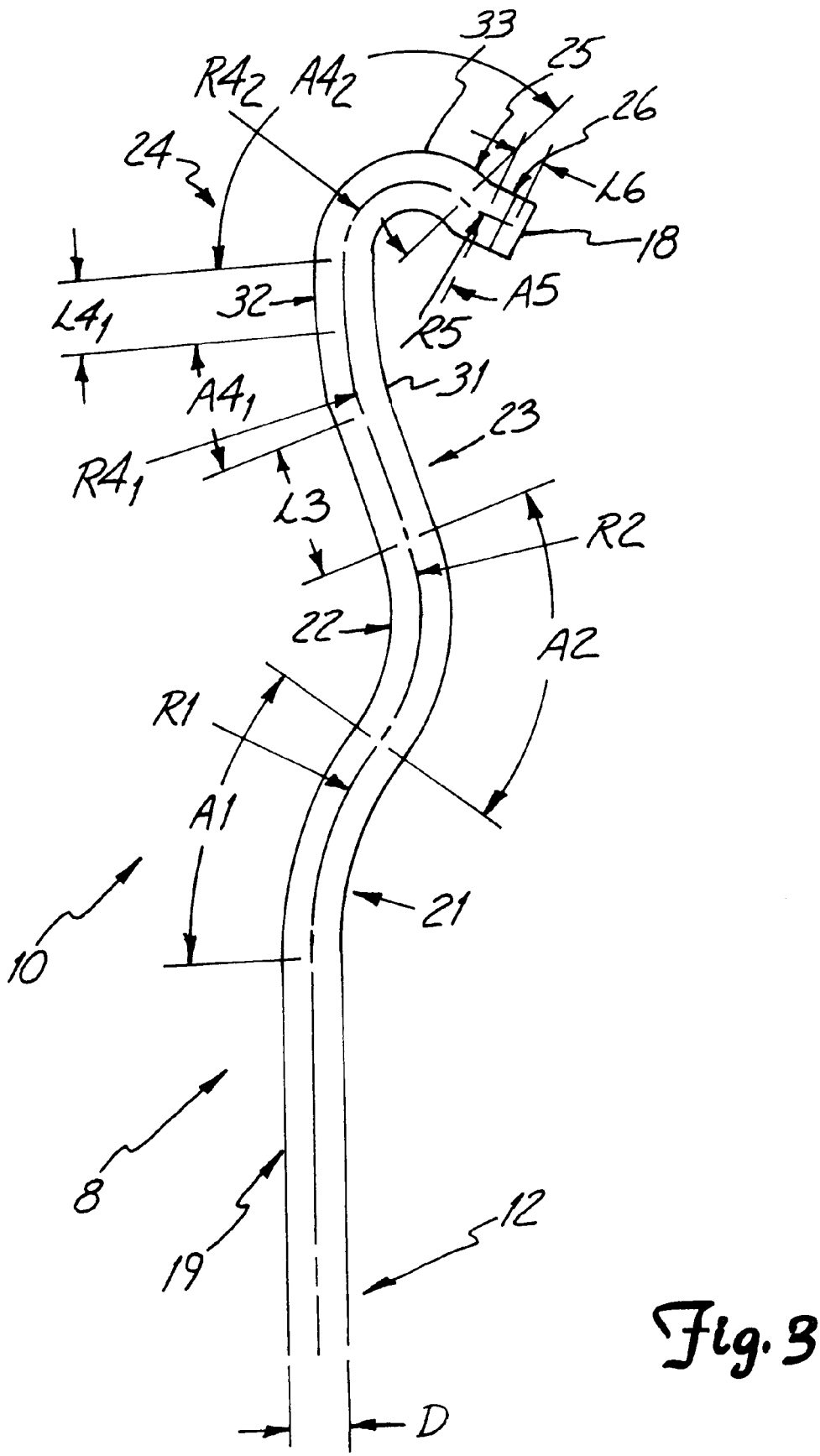
FIG. 3 is a detailed illustration of the stem of a first embodiment of the catheter shown in FIG. 1.
Figure 4:
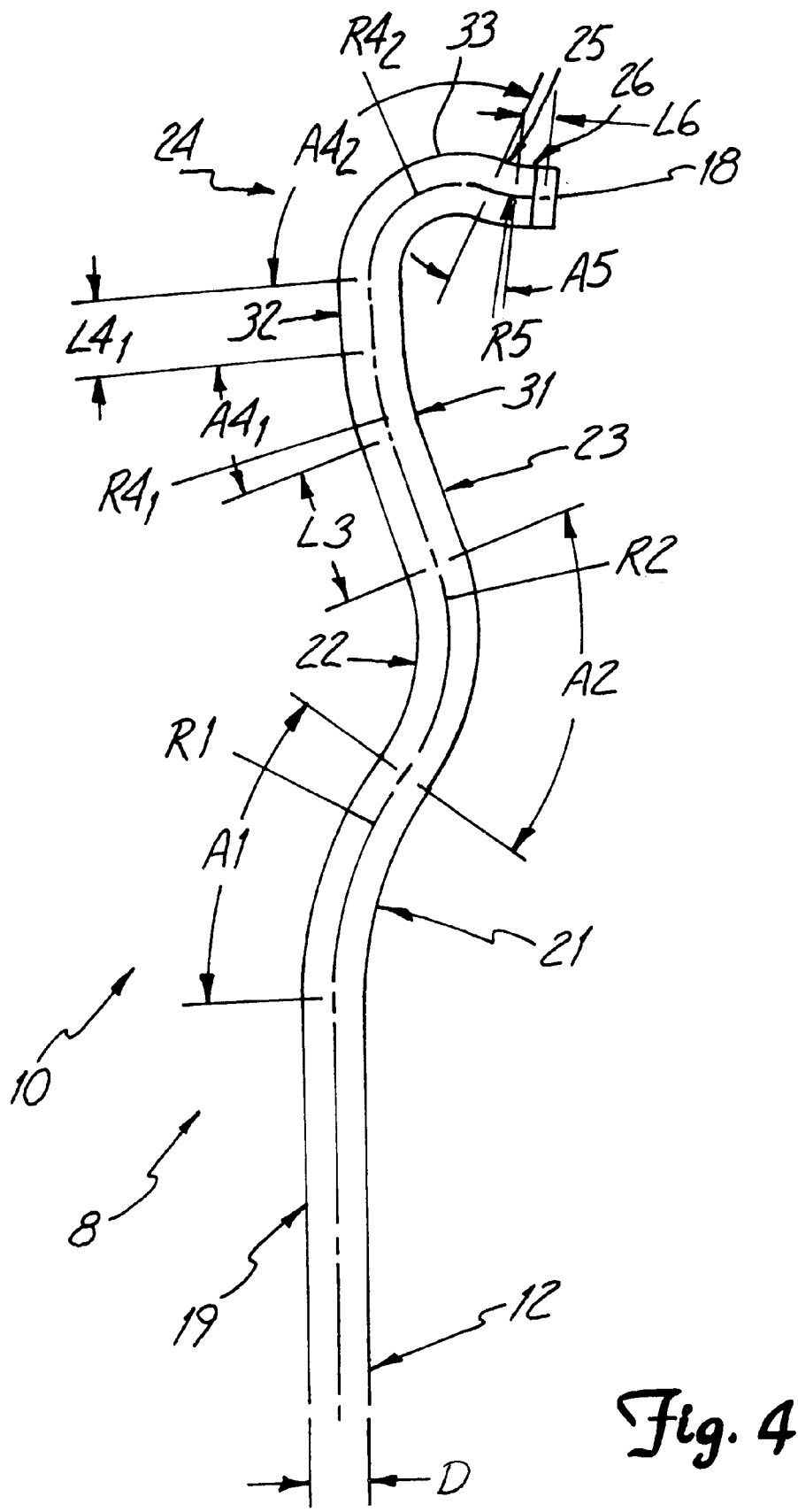
FIG. 4 is a detailed illustration of the stem of a second embodiment of the catheter shown in FIG. 1.

In the embodiments of stem 10 shown in FIGS. 3 and 4, the fourth arcuate section 24 includes a first arcuate subsection 31, a second linear subsection 32, and a third arcuate subsection 33. First arcuate subsection 31 is positioned between the third linear section 23 and tip 18 (i.e., is distally disposed from the third section), and has a free state arc length $A4_1$ and a free state radius $R4_1$. In the embodiment shown, first subsection 31 extends from and is contiguous with third linear section 23, having a proximal end connected directly to the distal end of the third linear section. Second linear subsection 32 is positioned between the first arcuate subsection 31 and tip 18 (i.e., is distally disposed from the first subsection), and has a free state length $L4_1$. In the embodiment shown, second subsection 32 extends from and is contiguous with the first subsection 31, having a proximal end connected directly to the distal end of the first subsection. Third arcuate subsection 33 is positioned between the second linear subsection 32 and tip 18 (i.e., is distally disposed from the second subsection), and has a free state arc length $A4_2$ and free state radius $R4_2$. In the embodiment shown, third subsection 33 extends from and is contiguous with the second subsection 32, having a proximal end connected directly to the distal end of the second subsection.

In the embodiments of the stem 10 shown in FIGS. 5–8, the fourth arcuate section 24 includes a first arcuate subsection 41 and a second arcuate subsection 42. First arcuate subsection 41 is positioned between the third linear section 23 and tip 18 (i.e., is distally disposed from the third section), and has a free state arc length $A4_1$ and a free state radius $R4_1$. In the embodiment shown, first subsection 41 extends from and is contiguous with third section 23, having a proximal end connected directly to the distal end of the third linear section. Second arcuate subsection 42 is positioned between the first arcuate subsection 41 and tip 18 (i.e., is distally disposed from the first subsection), and has a free state arc length $A4_2$ and a free state radius $R4_2$. In the embodiment shown, second subsection 42 extends from and is contiguous with first subsection 41, having a proximal end connected directly to the distal end of the first arcuate subsection.

Figure 7:
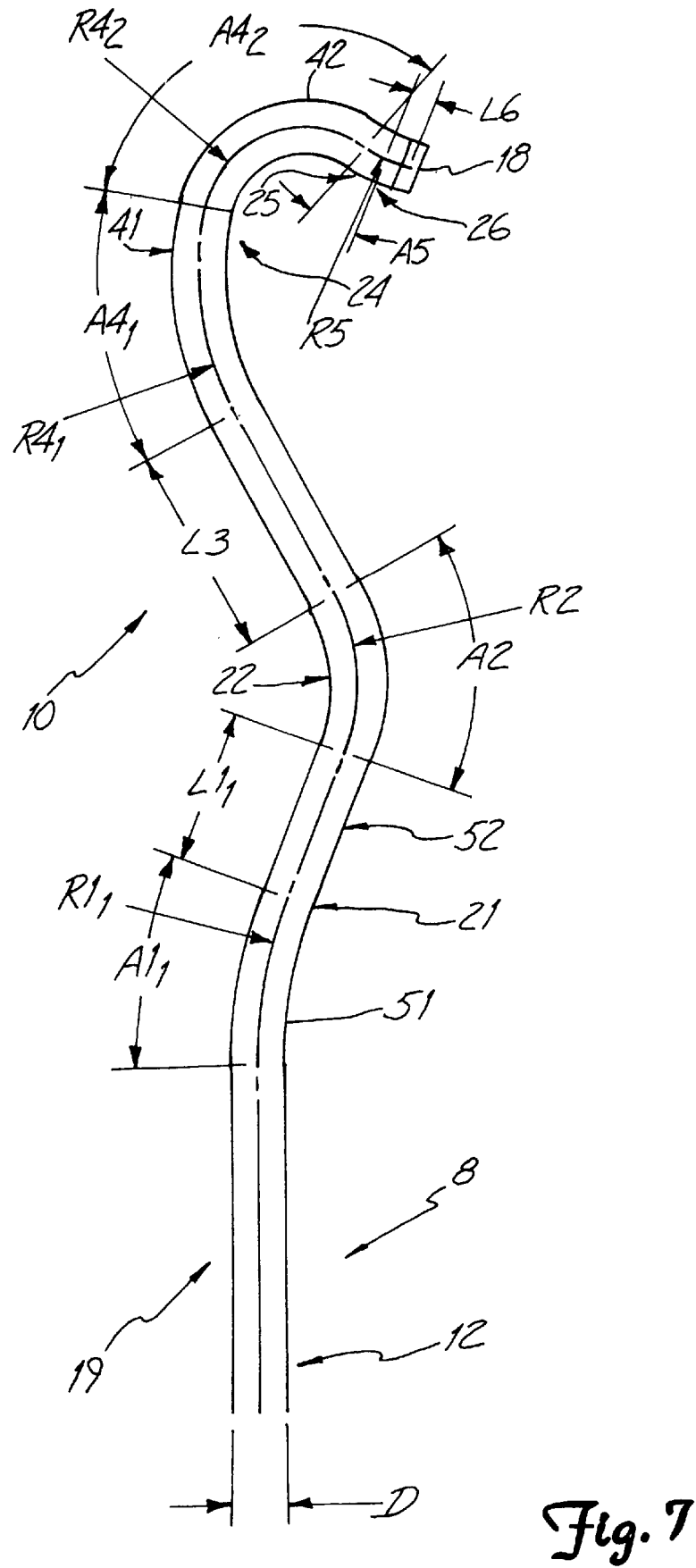
FIG. 7 is a detailed illustration of the stem of a fifth embodiment of the catheter shown in FIG. 1.
Figure 8:
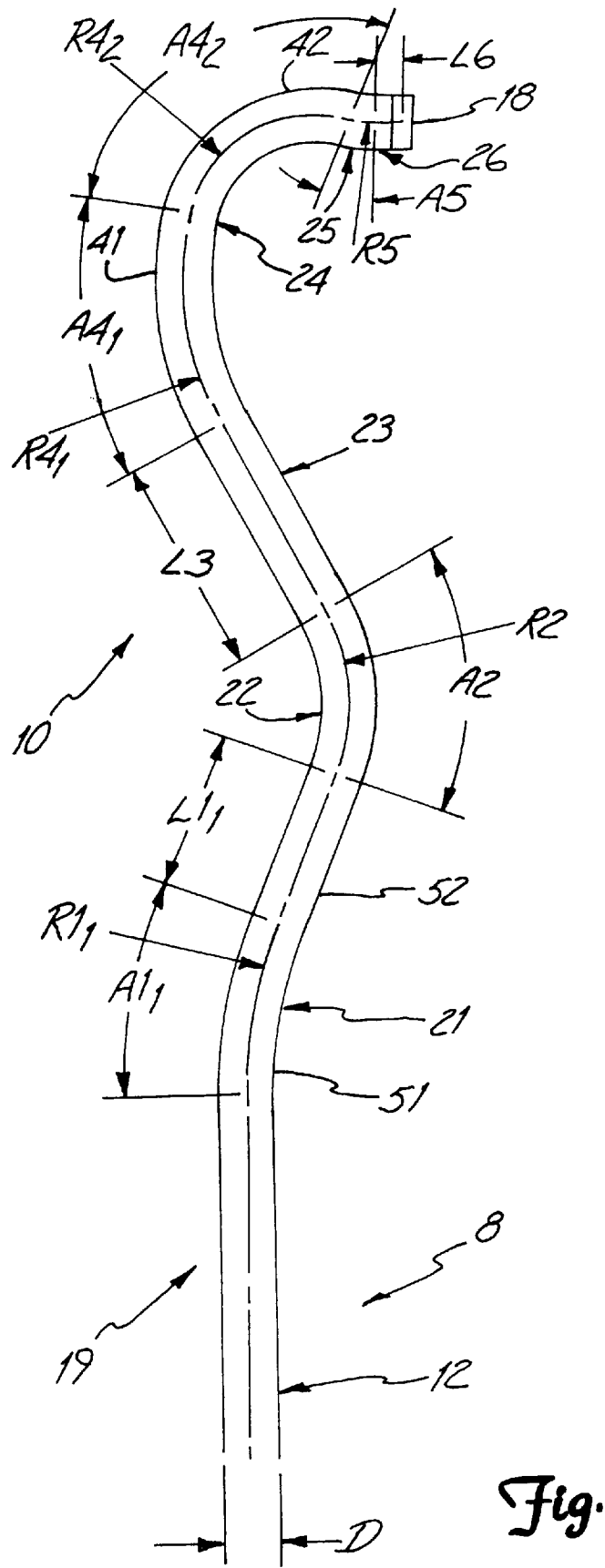
FIG. 8 is a detailed illustration of the stem of a sixth embodiment of the catheter shown in FIG. 1.

In the embodiments of stem 10 shown in FIGS. 7 and 8, the first arcuate section 21 includes a first arcuate subsection 51 and a second linear subsection 52. First arcuate subsection 51 is positioned between the linear section 19 of the stem 10 and tip 18 (i.e., is distally disposed from the linear section), and has a free state arc length $A1_1$ and a free state radius $R1_1$. In the embodiment shown, first subsection 51 extends from and is contiguous with linear section 19 of the stem 10, having a proximal end connected directly to the distal end of the linear section of the stem. Second linear subsection 52 is positioned between the first arcuate subsection 51 and tip 18 (i.e., is distally disposed from the first subsection), and has a free state length $L1_1$. In the embodiment shown, second subsection 52 extends from and is contiguous with the first subsection 51, having a proximal end connected directly to the distal end of the first subsection.

Second arcuate section 22 can be described as having a radius which is effectively in the opposite direction as the radius of first section 21, and extends away from the body stock 12 in the direction of an outwardly closing loop (i.e., extends or opens in a direction opposite that of the first section). Fourth arcuate section 24 can be described as having a radius which is in the same direction as the radius of the first section 21, and extends away from the second arcuate section and toward the body stock 12 in the direction of an inwardly closing loop (i.e., extends or opens in a direction opposite that of the second arcuate section). Fifth arcuate section 25 can be described as having a radius which is effectively in the opposite direction as the radius of the first section 21, and extends away from the body stock 12 in the direction of an outwardly closing loop. The combined length of the stem 10 and body stock 12 is often about 100 cm to 110 cm. When used in transradial applications, the combined length of stem 10 and body stock 12 can be about 125 cm. The length of stem 10, including the linear section 19, is often between about 22 cm and about 31 cm.

Figure 5:
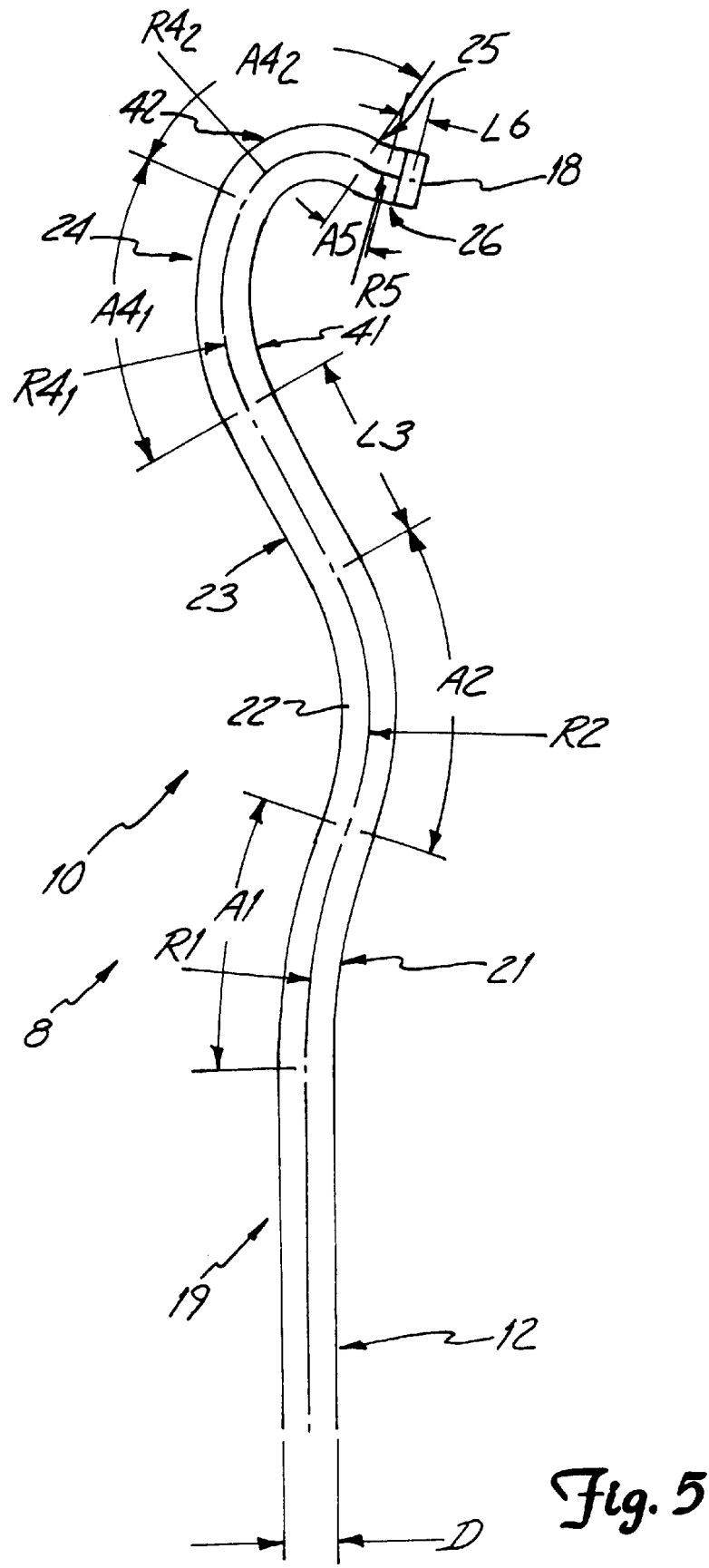
FIG. 5 is a detailed illustration of the stem of a third embodiment of the catheter shown in FIG. 1.
Figure 6:
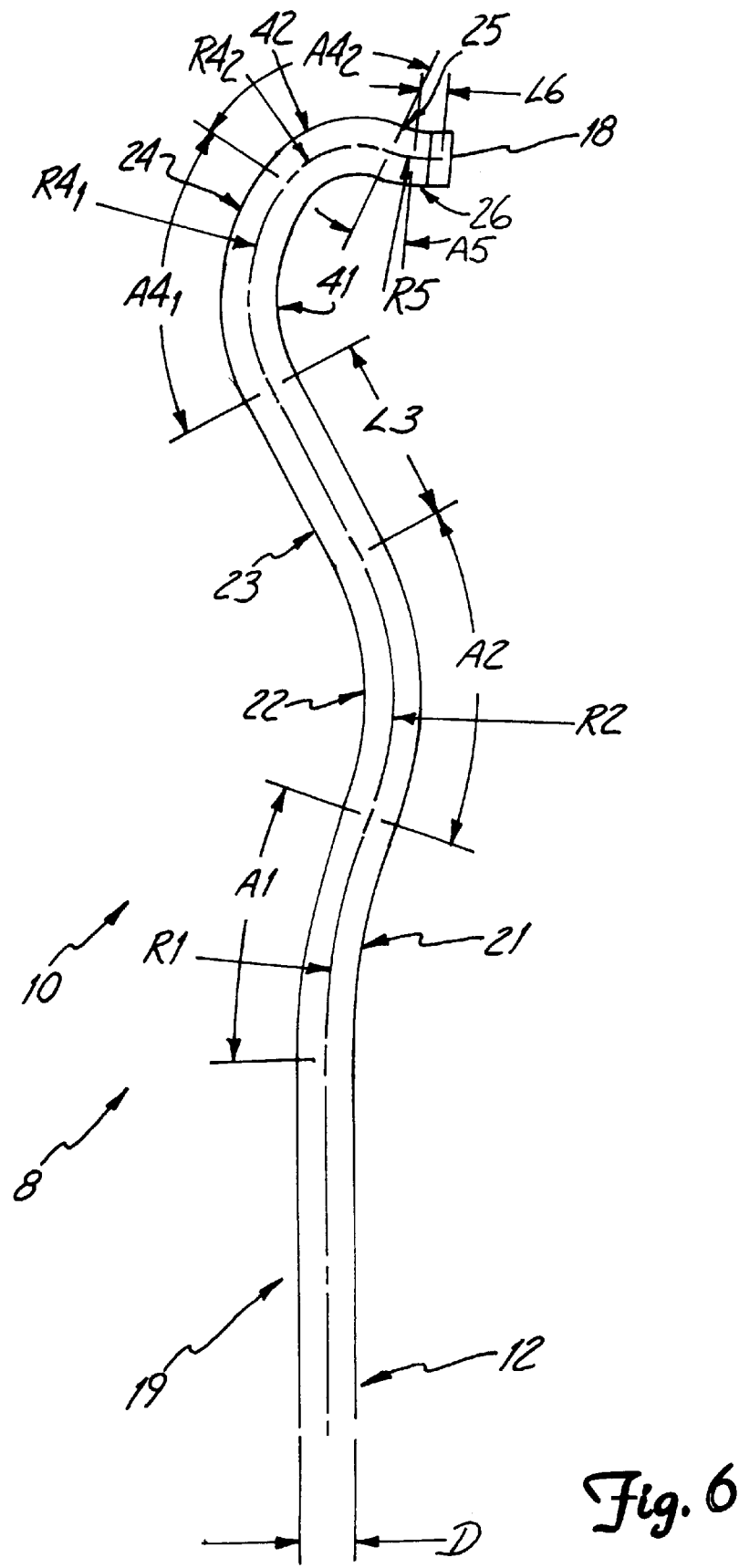
FIG. 6 is a detailed illustration of the stem of a fourth embodiment of the catheter shown in FIG. 1.

The arc lengths and radii of sections 21, 22, 24 and 25, the arc lengths, radii and lengths of the subsections of sections 21 and 24, and the length of sections 23 and 26, can vary on the basis of a number of factors including the size and characteristics of the coronary system of the patient with which the catheter 8 is intended to be used. The arc lengths, radii and distance lengths of preferred embodiments of the catheters shown in FIGS. 3–8 are listed below in Table 1. The catheter 8 shown in FIG. 4 is designed for use on patients having relatively small coronary systems with a normal or horizontal take-off of the right coronary artery. The catheter 8 shown in FIG. 5 is designed for use on patients having relatively average size coronary systems with a superior take-off (i.e., opening upwardly) of the right coronary artery ostium (i.e., the fifth section 25 orients the axis of tip 18 in a slightly upwardly extending direction when positioned in the coronary system of the patient). The catheter 8 shown in FIG. 7 is designed for use on patients having relatively large coronary systems with a superior take-off of the right coronary artery. The catheter 8 shown in FIG. 8 is designed for use on patients having relatively large coronary systems with a horizontal take-off. The catheter 8 shown in FIG. 3 is designed for use on patients having relatively small coronary systems with a superior take-off. The catheter 8 shown in FIG. 6 is designed for use on patients having relatively average size coronary systems with a horizontal take-off. Similarly, catheters having shapes similar to those shown in FIGS. 3–8 (but not shown) can be efficaciously sized and configured for patients having a range of coronary system sizes with different take-offs (e.g., including slightly downwardly extending tips for inferior take-offs).

TABLE 1

| EXAMPLE FIG. NO. | 3 | 4 | 5 | 6 | 7 | 8 |
|---|---|---|---|---|---|---|
| FIRST ARCUATE SECTION A1(°)/R1 (cm) | 38/4.45 | 38/4.45 | 22/8.89 | 22/8.89 | | |
| Arcuate Subsection $A1_1$(°)/$R1_1$ (cm) | | | | | 22/6.35 | 22/6.35 |
| Linear Subsection $L1_1$ (cm) | | | | | 2.24 | 2.24 |
| SECOND ARCUATE SECTION A2(°)/R2 (cm) | 57/2.79 | 57/2.79 | 49/4.45 | 49/4.45 | 50/2.79 | 50/2.79 |
| THIRD LINEAR SECTION L3(cm) | 1.78 | 1.78 | 2.72 | 2.72 | 3.15 | 3.15 |
| FOURTH ARCUATE SECTION A4(°)/R4 (cm) | | | | | | |
| 1st Arcuate Subsection $A4(°)/R4_1$ cm | 17/3.81 | 17/3.81 | 53/3.30 | 63/2.79 | 40/4.45 | 40/4.45 |
| Linear Subsection $L4_1$ (cm) | 0.97 | 0.97 | | | | |
| 2nd Arcuate Subsection $A4_2$(°)$R4_2$ (cm) | 140/0.91 | 118/1.07 | 100/1.14 | 80/1.14 | 120/1.42 | 100/1.70 |
| FIFTH ARCUATE SECTION A5(°)/R5 (cm) | 20/1.02 | 20/1.02 | 20/1.02 | 20/1.02 | 20/1.02 | 20/1.02 |
| SIXTH LINEAR SECTION L6 (cm) | 0.38 | 0.38 | 0.38 | 0.38 | 0.38 | 0.38 |

The arc lengths, radii and lengths of the sections and subsections of catheters in accordance with the present invention can vary on the basis of a number of factors including the size of the coronary system of the patient with which the catheter 8 is intended to be used. It is anticipated that an efficacious range of arc lengths $A1_1$ and $A1_1$ is between about 18° and 42°, with a particularly efficacious range being between about 22° and 38°. An expected efficacious range of radii R1 and $R1_1$ is about 4.0 and 10.0 cm (1.57 and 3.93 inch), with a particularly efficacious range being between about 4.45 and 8.89 cm (1.75 and 3.50 inch). An expected efficacious range of lengths $L1_1$ for the linear subsection 41 is between about 1.40 and 2.92 cm (0.55 and 1.15 inch), with a particularly efficacious range being between about 1.65 and 2.67 cm (0.65 and 1.05 inch)

It is anticipated that an efficacious range of arc lengths A2 for the second arcuate section 22 is between about 46° and 60°, with a particularly efficacious range being between about 49° and 57°. An anticipated efficacious range of radii R2 for the second arcuate section 22 is between about 2.25 and 5.10 cm (0.88 and 2.00 inch), with a particularly efficacious range being between about 2.79 and 4.45 cm (1.10 and 1.75 inch). An efficacious range of lengths L3 for third linear section 23 is between about 1.47 and 3.56 cm (0.58 and 1.40 inch), with a particularly efficacious range being between about 1.78 and 3.15 cm (0.70 and 1.24 inch).

An efficacious range of arc lengths $A4_1$ for the first arcuate subsection 31 or 41 of the fourth arcuate section 24 is between about 13° and 68° with a particularly efficacious range being between about 17° and 63°. An efficacious range of radii $R4_1$ for the first arcuate subsection 31 or 41 of the fourth arcuate section 24 is between about 2.80 and 5.10 cm (1.10 and 2.00 inch), with a particularly efficacious range being between about 3.30 and 4.45 cm (1.30 and 1.75 inch). An efficacious range of arc lengths $A4_2$ for the second arcuate subsection 33 or 42 of the fourth arcuate section 24 is between about 75° and 145°, with a particularly efficacious range being between about 80° and 140°. An efficacious range of radii $R4_2$ for the second arcuate subsection 33 or 42 of the fourth arcuate section 24 is between about 0.85 and 1.80 cm (0.33 and 0.71 inch), with a particularly efficacious range being between about 0.91 and 1.70 cm (0.36 and 0.68 inch). An expected efficacious range of lengths $L4_1$ for the linear subsection 32 is between about 0.75 and 1.25 cm (0.30 and 0.50 inch), with a particularly efficacious range being between about 0.85 and 1.10 cm (0.33 and 0.43 inch)

It is anticipated that an efficacious range of arc lengths A5 for the fifth arcuate section 25 is between about 15° and 26°, with a particularly efficacious range being between about 18° and 23°. An anticipated efficacious range of radii R5 for the fifth arcuate section 25 is between about 0.83 and 1.24 cm (0.33 and 0.49 inch), with a particularly efficacious range being between about 0.90 and 1.20 cm (0.35 and 0.47 inch). An efficacious range of lengths L6 for sixth linear section 26 is between about 0.30 and 0.50 cm (0.12 and 0.20 inch), with a particularly efficacious range being between about 0.33 and 0.46 cm (0.13 and 0.18 inch).

A patient's anatomy can be determined by radiographic analysis or other means. Based upon such an anatomy analysis, the catheter 8 which matches the anatomic characteristics of the patient can be selected.

Figure 9:
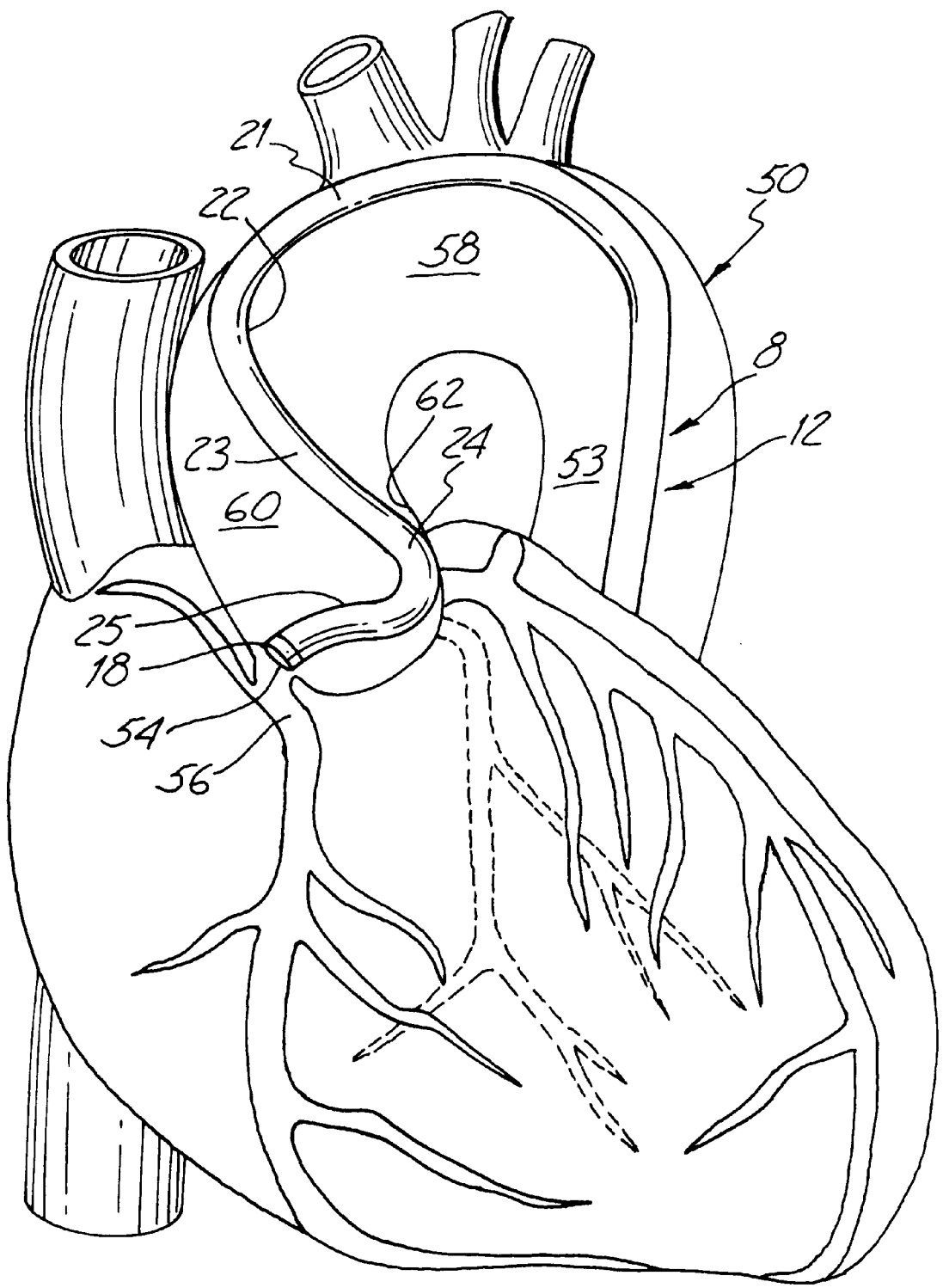
FIG. 9 is an illustration of a human heart with the catheter of the present invention positioned therein with its tip adjacent to the ostium of the right coronary artery.

FIG. 9 illustrates the shape and position of catheter 8 after it has been inserted into an aorta 50 of a patient. As shown, after being inserted through the patient's femoral artery, the stem 10 enters aorta 50 through the descending aorta 53 and engages ostium 54 of the right coronary artery 56 (e.g., at least the distal end of the catheter is within the ostium) after passing through the aortic arch 58 and into the ascending aorta 60. During catheterization procedures the distal end is often extended about 5 mm into the ostium. As shown, a length of stem 10 including first arcuate section 21 is engaged with a continuous length of the upper wall of the aortic arch 58 (e.g., a length of at least about 2 cm). As the stem 10 approaches and extends downwardly in the ascending aorta 60, the second arcuate section 22 causes the stem to be directed across the ascending aorta 60 and toward the contralateral wall 62 of the right coronary artery (i.e., the wall of the aorta opposite the ostium of the right coronary artery). The portion of the stem 10 including second arcuate section 22 which causes the stem to be directed from the upper wall of the aortic arch toward the contralateral wall is sometimes referred to as the "secondary curved section." Third linear section 23 extends across the ascending aorta 60. A portion of the stem 10 including at least a portion of the fourth arcuate section 24 is engaged with a continuous length of the contralateral wall 62 at a location adjacent to the ostium of the left coronary artery. The portion of the fourth arcuate section 24 which engages the contralateral wall will typically engage at least a portion of the contralateral wall adjacent to and above the ostium of the left coronary artery. The portion of the stem 10 including the fourth arcuate section which engages the contralateral wall and directs the end section of the stem across the ascending aorta is sometimes referred to as the "primary curved section." A portion of the stem 10 including at least a portion of the fifth arcuate section 25 extends from the contralateral wall 62 toward the ostium 54 of the right coronary artery 56 to position the tip 18 of the stem in engagement with the ostium in a coaxially aligned manner. As shown in FIG. 9, the portion of the stem 10 which extends from the contralateral wall toward the ostium of the right coronary artery performs this function while being suspended above (i.e., without engaging) the cup-shaped left and/or right coronary cusps at the base of the ascending aorta 60.

Catheters 8 including stems 10 in accordance with the present invention offer considerable advantages. The catheter can be quickly and efficiently inserted while at the same time accurately positioning the tip or distal end of the stem in coaxial engagement with the ostium of the right coronary artery. Similarly, the catheter can be efficiently removed. The coaxial alignment of the tip within the ostium facilitates the insertion of interventional devices and minimizes risk of trauma to the artery. Since the stem backs-up (i.e., is engaged with) the contralateral wall of the ascending aorta along a significant portion of its length beginning at a location generally opposite the aorta from the ostium of the right coronary artery, it provides a stable platform for deploying interventional devices and will support relatively high deployment forces. The back-up provided by the engagement of the portions of the stem 10 with the upper wall of the aortic arch 58 enhances this deployment capability.

Although the preferred embodiments of the catheter stem 10 have been described as having contiguous arcuate and linear sections, relatively short intervening sections having different lengths and/or radii (e.g., the variations in the fourth arcuate section 24 between the embodiments shown in FIGS. 3 and 5 and the variations in the first arcuate section 21 between the embodiments shown in FIGS. 6 and 7) could be included between the described sections while providing substantially the same characteristics and advantages described herein.

The materials from which catheter 8, including stem 10, are fabricated, and other characteristics of the catheter such as the inner and outer diameters of the stem and body stock 12, can be similar or identical to known or otherwise conventional catheters. In one embodiment, the outer diameter D of the catheters shown in FIG. 3–8 is 8 French (about 0.27 cm (0.105 inch)). The above-described shapes of stem 10 can be (without limitation) incorporated into Guidezilla® guide catheters and/or Schneider Guider® guide catheters available from Schneider (USA) Inc, of Minneapolis, Minn. Other catheters which can include the shapes of stem 10 are disclosed in U.S. Pat. No. 5,599,325 and application Ser. Nos. 08/645,381 and 08/647,606, both of which were filed on May 13, 1996. The documents referred to above are hereby incorporated by reference in their entirety and for all purposes.

The hardness of the polymer materials incorporated into stem 10 and body stock 12 typically vary over the length of catheter 8. As shown in FIG. 1, for example, the hardness of a distal most end portion A of stem 10 including tip 18 and at least a portion of fifth arcuate section 25 (e.g., a length of about 5 mm) is a durometer of about 30 Shore D. The hardness of a relatively short portion B (e.g., a length of about 5 mm) including portions of fifth arcuate section 25 and/or fourth arcuate section 24 is a durometer of about 46 Shore D. The hardness of the remaining portion C of stem 10 is a durometer of about 63 Shore D. Body stock 12 can have a hardness which is greater than that of stem 10 so as to be less flexible than the stem.

Although the present invention has been described with reference to preferred embodiments, those skilled in the art will recognize that changes can be made in form and detail without departing from the spirit and scope of the invention.

What is claimed is:

1. A femoral approach right coronary artery catheter configured to be directed to an ostium of a patient's right coronary artery through an aortic arch and ascending aorta, comprising a flexible tubular body stock having a distal end and a nonlinear stem extending from the distal end of the body stock, the stem including a distal end, a primary curved section having one or more free state radii and a free state arc length and positioned between the distal ends of the stem and body stock, and a secondary curved section having one or more free state radii and a free state arc length and positioned between the primary curved section and the distal end of the body stock and extending in a direction generally opposite the direction of the primary curved section, and wherein the radii and lengths of the stem including the primary and secondary curved sections are adapted to cause a portion of the stem between the secondary curved section and the distal end of the body stock to engage a continuous length of the upper wall of the aortic arch, to cause the secondary curved section to direct the stem generally downwardly and across the ascending aorta toward a contralateral wall opposite the ostium of the right coronary artery, and to cause the primary curved section to engage the contralateral wall at a location adjacent to the ostium of the left coronary artery and to direct an end section of the stem across the ascending aorta toward the ostium of the right coronary artery, when the catheter is positioned within the patient with the distal end of the stem engaged with the ostium of the right coronary artery.

2. The right coronary catheter of claim 1 wherein the primary curved section includes an arc length between about 120 and 175 degrees.

3. The right coronary catheter of claim 2 wherein the primary curved section includes one or more radii of curvature between about 0.91 and 4.45 cm.

4. The right coronary catheter of claim 1 wherein the primary curved section includes one or more radii of curvature between about 0.91 and 4.45 cm.

5. The right coronary catheter of claim 1 wherein the secondary curved section includes an arc length between about 46 and 60 degrees.

6. The right coronary catheter of claim 5 wherein the secondary curved section has a radius of curvature between about 2.25 and 5.10 cm.

7. The right coronary catheter of claim 1 wherein the secondary curved section has a radius of curvature between about 2.25 and 5.10 cm.

8. The right coronary catheter of claim 1 wherein:
the primary curved section includes an arc length between about 120 and 175 degrees and has one or more radii of curvature between about 0.91 and 4.45 cm; and
the secondary curved section includes an arc length between about 46 and 60 degrees and has one or more radii of curvature between about 2.25 and 5.10 cm.

9. The right coronary catheter of claim 8 and including an arcuate section disposed distally from a distal end of the primary curved section and extending in a direction generally opposite the direction of the primary curved section, wherein the arcuate section includes an arc length between about 15 and 26 degrees and has one or more radii of curvature between about 0.83 and 1.24 cm.

10. The right coronary catheter of claim 8 and including an arcuate section disposed between the body stock and the secondary curved section and extending in a direction generally opposite the direction of the secondary curved section, wherein the arcuate section includes an arc length between about 18 and 42 degrees and has a radius of curvature between about 4.0 and 10.0 cm.

11. The right coronary catheter of claim 8 and including a linear section disposed between the primary and secondary curved sections, wherein the linear section has a length between about 1.47 and 3.56 cm.

12. The right coronary catheter of claim 1 wherein the primary curved section is adapted to direct the end section of the stem across the ascending aorta without contacting the right and/or left coronary cusps.

13. The right coronary catheter of claim 1 wherein at least a portion of the primary curved section has a flexibility which is greater than a flexibility of the secondary curved section.

14. A right coronary artery catheter comprising a flexible tubular member having a body stock and a stem extending from a distal end of the body stock, the stem including:
a first arcuate section having a first free state radius and a first free state arc length disposed distally from the distal end of the body stock;
a second arcuate section having a second free state radius and a second free state arc length disposed distally from a distal end of the first section away from the body stock;
a third linear section having a third length and disposed distally from a distal end of the second section;
a fourth arcuate section having a fourth free state radius and a fourth free state arc length disposed distally from a distal end of the third section toward the body stock; and
a fifth arcuate section having a fifth free state radius and a fifth free state arc length disposed distally from a distal end of the fourth section away from the body stock.

15. The right coronary catheter of claim 14 wherein:
the second arcuate section has a second radius between about 2.25 and 5.10 cm and a second arc length between about 46 and 60 degrees;
the third linear section has a length between about 1.47 and 3.56 cm; and
the fourth arcuate section has a fourth radius between about 0.91 and 4.45 cm and a fourth arc length between about 120 and 175 degrees.

16. The right coronary catheter of claim 15 wherein the fourth arcuate section includes:
a first arcuate subsection having a free state radius and a free state arc length disposed distally from a distal end of the third linear section; and
a second arcuate subsection having a free state radius which is less than the free state radius of the first subsection, and a free state arc length which is greater than the arc length of the first subsection disposed distally from a distal end of the first arcuate subsection, wherein a sum of the free state radii of the first and second subsections is between about 120 and 175 degrees.

17. The right coronary catheter of claim 16 wherein:
the first arcuate subsection has a radius between about 2.79 and 4.45 cm and an arc length between about 17 and 63 degrees; and
the second arcuate subsection has a radius between about 0.91 and 1.70 cm and an arc length between about 80 and 140 degrees.

18. The right coronary catheter of claim 17 wherein the fourth arcuate section further includes a linear subsection having a length between about 0.75 and 1.25 cm between the first and second arcuate subsections.

19. The right coronary artery catheter of claim 16 wherein the fourth arcuate section further includes a linear subsection between the first and second arcuate subsections.

20. The right coronary catheter of claim 15 wherein the fifth arcuate section has a fifth radius between about 0.83 and 1.24 cm and an arc length between about 15 and 26 degrees.

21. The right coronary catheter of claim 15 wherein the first arcuate section has a first free state radius between about 4.0 and 10.0 cm and an arc length between about 18 and 42 degrees.

22. The right coronary catheter of claim 21 wherein the first arcuate section includes a linear subsection having a length between about 1.40 and 2.92 cm.

23. The right coronary catheter of claim 14 wherein:

the second arcuate section has a second radius between about 2.79 and 4.45 cm and a second arc length between about 49 and 57 degrees;

the third linear section has a length between about 1.78 and 3.15 cm; and the fourth arcuate section has a fourth radius between about 0.91 and 4.45 cm and a fourth arc length between about 135 and 160 degrees.

24. The right coronary catheter of claim 23 wherein the fourth arcuate section includes:

a first arcuate subsection having a free state radius and a free state arc length disposed distally from a distal end of the third linear section; and a second arcuate subsection having a free state radius which is less than the free state radius of the first subsection, and a free state arc length which is greater than the arc length of the first subsection disposed distally from a distal end of the first arcuate subsection, wherein a sum of the free state radii of the first and second subsections is between about 135 and 160 degrees.

25. The right coronary catheter of claim 24 wherein:

the first arcuate subsection has a radius between about 2.79 and 4.45 cm and an arc length between about 17 and 63 degrees; and the second arcuate subsection has a radius between about 0.91 and 1.70 cm and an arc length between about 80 and 140 degrees.

26. The right coronary catheter of claim 25 wherein the fourth arcuate section further includes a linear subsection having a length between about 0.85 and 1.10 cm between the first and second arcuate subsections.

27. The right coronary artery catheter of claim 24 wherein the fourth arcuate section further includes a linear subsection between the first and second arcuate subsections.

28. The right coronary catheter of claim 23 wherein the fifth arcuate section has a fifth radius between about 0.90 and 1.20 cm and an arc length between about 18 and 23 degrees.

29. The right coronary catheter of claim 23 wherein the first arcuate section has a first free state radius between about 4.45 and 8.89 cm and an arc length between about 22 and 38 degrees.

30. The right coronary catheter of claim 29 wherein the first arcuate section includes a linear subsection having a length between about 1.65 and 2.67 cm.

31. A right coronary artery catheter comprising a flexible tubular member having a body stock and a stem extending from a distal end of the body stock, the stem including:

a first arcuate section having a first free state radius between about 4.45 and 8.89 cm and a first free state arc length between about 22 and 38 degrees disposed distally from the distal end of the body stock;

a second arcuate section having a second free state radius between about 2.79 and 4.45 cm and a second free state arc length between about 49 and 57 degrees disposed distally from a distal end of the first section away from the body stock;

a third linear section having a third length between about 1.78 and 3.15 cm disposed distally from a distal end of the second section;

a fourth arcuate section disposed distally from a distal end of the third section toward the body stock, including a first arcuate subsection having a free state radius between about 2.79 and 4.45 cm and a free state arc length between about 17 and 63 degrees disposed distally from a distal end of the third linear section; and a second arcuate subsection having a free state radius between about 0.91 and 1.70 cm and a free state arc length between about 80 and 140 degrees disposed distally from a distal end of the first arcuate subsection; and a fifth arcuate section having a fifth free state radius between about 0.90 and 1.20 cm and a fifth free state arc length between about 18 and 23 degrees disposed distally from a distal end of the fourth section away from the body stock.

32. The right coronary catheter of claim 31 and further including a tip on a distal end of the fifth arcuate section.

* * * * *